(12) United States Patent
Suzuki

(10) Patent No.: US 6,399,815 B2
(45) Date of Patent: Jun. 4, 2002

(54) PROCESS FOR PREPARING A SULFINATE

(75) Inventor: Takatugu Suzuki, Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/891,434

(22) Filed: Jun. 26, 2001

(30) Foreign Application Priority Data

Jul. 6, 2000 (JP) ........................................ 2000/204872

(51) Int. Cl.$^7$ ........................................... C07C 313/02
(52) U.S. Cl. ................................................... 562/125
(58) Field of Search ................................. 562/125, 126

(56) References Cited

U.S. PATENT DOCUMENTS

| | | | | |
|---|---|---|---|---|
| 4,831,194 A | * | 5/1989 | Kreidl et al. | 568/36 |
| 5,008,448 A | * | 4/1991 | Brown | 562/429 |
| 5,157,150 A | * | 10/1992 | Brown | 562/125 |
| 6,258,984 B1 | * | 7/2001 | Folz et al. | 568/28 |

OTHER PUBLICATIONS

Chemical Abstracts XP–002179907, 1989.
Chemical Abstracts, Columbus Ohio XP–002179906, 1989
CA:110:25251 XP–002166855. J. Med. Chem. 1997, 40. 1018–1025.

* cited by examiner

*Primary Examiner*—Jean F. Vollano
(74) *Attorney, Agent, or Firm*—Bierman, Muserlian and Lucas

(57) ABSTRACT

Disclosed is a process to prepare a sulfinate, which is useful for preparing a synthetic intermediate of an organic compound, especially for a color coupler, characterized by reducing a sulfonyl chloride with a sulfite or a hydrogensulfite in the presence of a hydrogenphosphate.

18 Claims, No Drawings

PROCESS FOR PREPARING A SULFINATE

FIELD OF THE INVENTION

This invention is related to a process for preparing a sulfinate which is useful for a synthetic intermediate of an organic compound.

BACKGROUND OF THE INVENTION

It is common practice that sulfones be synthesized by oxidation of sulfides or sulfoxides, by alkylation of salts of sulfinic acids, by a Friedel-Crafts reaction between aromatic compounds and sulfonyl halides, by dehydrated condensation of aromatic compounds with sulfonic acids, by a reaction of Grignard reagents and esters of sulfonic acids, or by an addition of sulfonyl halides or sulfinic acids to unsaturated compounds. Of these reactions, oxidation of sulfides or sulfoxides and alkylation of salts of sulfinic acids are frequently used because they produce sulfones at a high yield. Said oxidation of sulfides or sulfoxides gives results in a high reaction yield. But unfortunately, multi-step reactions are needed to synthesize said sulfides or said sulfoxides used as raw materials and, at the same time, said sulfides or sulfoxides give off a strongly unpleasant odor. In effect, the use of this reaction has several drawbacks in respect to environmental aspect, handling aspect, and cost. In contrast to this reaction, said alkylation of salts of sulfinic acids is superior to the other preparation methods from an industrial point of view, because said salts of sulfinic acids can be synthesized with comparative ease and they have no unpleasant odor.

It is also common practice that sulfinic acids or their salts be synthesized by reduction of sulfonyl chlorides and by a reaction of sulfur dioxide with Grignard reagents or diazonium salts. Of these reactions, reduction of sulfonyl chlorides is most widely used. The reducing reagents for sulfonyl chlorides can be selected from: Zn(F. C. Whitmore, et al., Org. Synth., I, 492 (1941)); sodium sulfite(S. Smiles, et al, Org. Synth., I, 7 (1941)); sodium hydrogensulfite(R. Mercanton, et al., Helv. Chim. Acta., 28, 538 (1945)); or sodium sulfide(E. Fromm, et al., Ber., 42, 3821 (1909)). Of these reagents, sodium sulfite or sodium hydrogensulfite are often used and reaction yields are quite satisfactory.

It is well known that free sulfinic acids are unstable, and also that they disproportionate in solid or in solution to produce thiosulfonates and sulfonic acids. On the other hand, salts of sulfinic acids are so stable that they are suitable to be handled in the industrial settings. Neutralization of sulfinic acids obtained by the reduction of the above-mentioned sulfonyl chlorides with inorganic bases is commonly used to synthesize sulfinic acids. As for inorganic bases, sodium hydroxide and sodium hydrogencarbonate are often used. However, when sodium hydroxide is used, sulfonic acids are formed as by-products due to its strong alkalinity. And, when sodium hydrogensulfite is used, carbon dioxide is vigorously produced during neutralization and is quite hazardous. This invention is expected to further improve the process to overcome these synthetic problems in the industry.

Photographic couplers are commonly used in silver halide color photosensitive materials. Said couplers having a sulfonyl group are widely used, such as in unexamined and published Japanese Patent Application Nos. 10-97039 and 2000-19697. Couplers having sulfonyl groups show good color forming reactivity, good color reproduction quality, and good image stability, all of which are important photographic properties, and they are thus suitable for photographic color couplers.

One of the common methods to introduce sulfonyl groups into photographic couplers is to react acid chlorides containing sulfonyl groups with coupler residues containing amino groups in the presence of base catalysts. But, the reaction selectivity of acid chlorides towards amino groups is small due to a high reactivity of acid chlorides, and this will cause a decrease in yield as well as in purity of the product. At the same time, acid chlorides must be handled with extreme care because they are highly corrosive.

SUMMARY THE INVENTION

This invention is presented to solve the above problems. The object of the present invention is to provide a process for preparing a sulfinate which is useful for a synthetic intermediate of an organic compound as well as for a photographic coupler of high yield, high purity, and with ease of production. Another object of this invention is to provide a process for preparing a photographic coupler by the use thereof, again of high yield and ease of production.

The object of the present invention can be achieved by the following processes.

(1) A process for preparing a sulfinate through reduction of a sulfonyl chloride with a sulfite or a hydrogensulfite, in the presence of a hydrogenphosphate.

(2) The process of the above-mentioned process (1) wherein the reduction is accomplished in a mixture of at least one organic solvent and water.

(3) The process of the above-mentioned process (1) wherein the sulfinate is represented by Formula (I), $$R_1SO_2M \qquad \text{Formula (I)}$$

wherein $R_1$ is an aryl group ; M is a sodium atom or a potassium atom.

(4) The process of the above-mentioned process (1) wherein said sulfonyl chloride is represented by Formula (II), $$R_1SO_2Cl \qquad \text{Formula (II)}$$

wherein $R_1$ is an aryl group.

(5) The process of the above-mentioned process (3) wherein said sodium sulfinate and said potassium sulfinate represented by Formula (I) is one selected from the group consisting of I-1 to I-15.

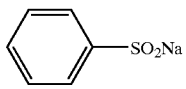

I-1

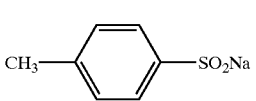

I-2

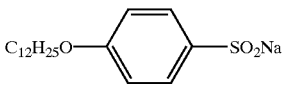

I-3

I-4

-continued

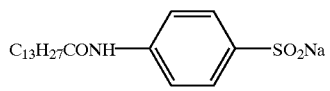
I-5

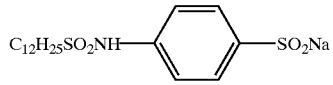
I-6

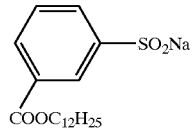
I-7

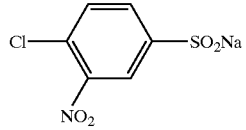
I-8

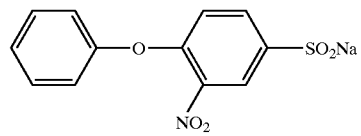
I-9

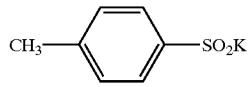
I-10

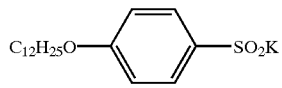
I-11

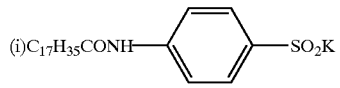
I-12

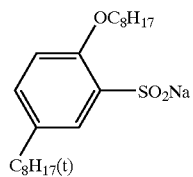
I-13

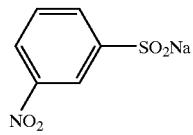
I-14

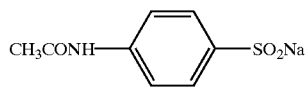
I-15

(6) The process of the above-mentioned process (4) wherein said sulfonyl chloride represented by Formula (II) is one selected from the group consisting of II-1 to II-14.

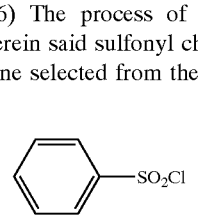
II-1

-continued

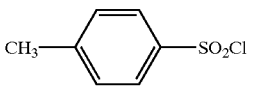
II-2

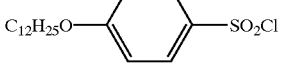
II-3

II-4

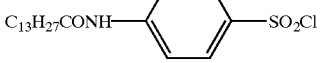
II-5

II-6

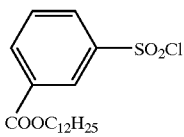
II-7

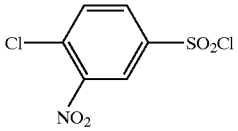
II-8

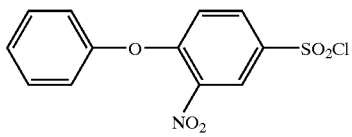
II-9

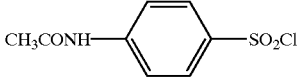
II-10

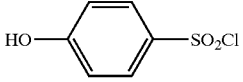
II-11

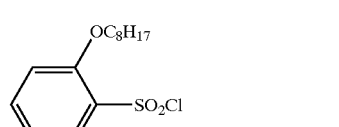
II-12

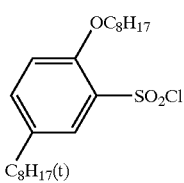
II-13

II-14

(7) The process of the above-mentioned process (2) wherein the organic solvent is one selected from the group consisting of methanol, ethanol, isopropanol, butanol, tert-butanol, acetonitrile, ethyl acetate, toluene, dichloromethane, tetrahydrofuran, acetone, and N,N-dimethylformamide.

(8) The process of the above-mentioned process (7) wherein the organic solvent is one selected from the group consisting of ethanol, isopropanol, tert-butanol, and acetonitrile.

DETAILED DESCRIPTION OF THE INVENTION

The present invention is detailed below. The sulfinate, the sulfite, the hydrogensulfite, and the hydrogenphosphate of the present invention comprise a cation of a metal or an ammonium in their molecular structure. Preferably, said cation of a metal or an ammonium is one selected from the group consisting of $Na^+$, $K^+$, $Li^+$, $Mg^{++}$, $Ca^{++}$, $NH_4^+$. And more preferably said cation of a metal is $Na^+$ or $k^+$.

Disodium hydrogenphosphate, used in the present invention, is also known as sodium secondary phosphate, disodium phosphate, or sodium dibasic phosphate. It exists in the form of an anhydrous state or with water of crystallization. Dipotassium hydrogenphosphate is also known as potassium secondary phosphate or dipotassium phosphate.

Disodium hydrogenphosphate and dipotassium hydrogenphosphate used in the present invention may be prepared by neutralizing phosphoric acid with either sodium hydroxide, sodium carbonate, potassium hydroxide, or potassium carbonate and further may be used in a buffer solution of pH 9–10.

The sodium sulfinate or potassium sulfinate prepared in the present invention can contain water of crystallization. In case when free sulfinic acids are stable, one can neutralize the sodium sulfnates or potassium sulfinates with mineral acids to isolate the free sulfinic acids.

Sodium sulfite used in the present invention is also known as soda sulfite, and both an anhydrous salt and a water-of-crystallization containing salt are known. Sodium hydrogensulfite is also known as sodium bisulfite or sodium acid sulfite. Sodium sulfite is commercially available in a mixture of sodium hydrogensulfite and sodium pyrosulfite and can be used in the present invention. Potassium sulfite is also known as potassium kali and it is commercially available in a mixture of potassium hydrogensulfite and potassium pyrosulfite and can also be used in the present invention.

When a sodium sulfinate or a potassium sulfinate is prepared by reducing a sulfonyl chloride with either sodium sulfite, sodium hydrogensulfite, potassium sulfite, or potassium hydrogensulfite in the presence of disodium hydrogenphosphate or potassium hydrogenphosphate, sodium salts and potassium salts may as well be used without admixing. Preferred preparation methods are: (1) to prepare a sodium sulfinate by reducing a sulfonyl chloride with either sodium sulfite or sodium hydrogensulfite in the presence of disodium hydrogenphosphate; or (2) to prepare a potassium sulfinate by reducing a sulfonyl chloride with either potassium sulfite or potassium hydrogensulfite in the presence of dipotassium hydrogenphosphate. When considering solubility of the sulfonyl chloride and the inorganic salts such as disodium hydrogenphosphate, dipotassium hydrogenphosphate, sodium sulfite, sodium hydrogensulfite, potassium sulfite, or potassium hydrogensulfite, which are used as starting materials in the present invention, it is preferable to accomplish the reaction in a mixture of an organic solvent and water.

The organic solvent used in this invention can be water-miscible or water-immiscible. More specifically, one can use an organic solvent such as, methanol, ethanol, isopropanol, butanol, tert-butanol, acetonitrile, ethyl acetate, toluene, dichloromethane, tetrahydrofuran, acetone, and N,N-dimethylformamide. Of these, water miscible solvents are preferred. More specifically, the preferred solvents are ethanol, isopropanol, tert-butanol, and acetonitrile. When a mixture of an organic solvent and water is used in this invention, the volume ratio of an organic solvent to water is usually between 1:100 and 100:1,. More preferred volume ratio is between 1:20 and 20:1. And still more preferred volume ratio is between 1:10 and 1:1.

The reaction temperature of the present invention is usually 0–100° C., but 10–50° C. is preferred and 15–45° C. is more preferred.

The amount of disodium hydrogenphosphate and dipotassium hydrogenphosphate is preferably 1.5–4.5 times of mole of the used sulfonyl chloride. More specifically, 2.0–4.0 times of mole are more preferred.

The amount of sodium sulfite, sodium hydrogensulfite, potassium sulfite, and potassium hydrogensulfite used in the present invention is preferably 1.0–3.0 times of mole of the used sulfonyl chloride. More specifically, 1.5–2.5 times of moles are more preferred.

The aryl group represented by $R_1$ in Formula (I) and Formula (II) of the invention includes a phenyl group and a naphthyl group. Of them, the phenyl group is preferred.

The aryl group represented by $R_1$ can be replaced with a substituent, and there is no limitation for said substituent. For instance, the following substituents can be used; an alkyl group, a cycloalkyl group, an aryl group, an anilino group, an acylamino group, a sulfonamide group, an alkylthio group, an arylthio group, an alkenyl group, a halogen atom, an cycloalkenyl group, an alkynyl group, a heterocylic group, a sulfonyl group, a phosphonyl group, an acyl group, a carbamoyl group, a sulfamoyl group, a cyano group, an alkoxy group, an aryloxy group, a heterocycle-oxy group, a siloxy, an acyloxy group, a sulfonyloxy group, a carbamoyloxy group, an amino group, an alkylamino group, an imido group, an ureido group, a sulfamoylamino group, an alkoxycarbonylamino group, an aryloxycarbonylamino group, an alkoxycarbonyl group, an aryloxycarbonyl group, a heterocycle-thio group, a thioureido group, a carboxy group, a hydroxy group, a mercapto group, a nitro group, and a sulfo group.

The aryl group represented by $R_1$ preferably has a substituent. More preferable is a substituent having an alkyl group with a carbon atom number of 8–21. The substituent of the aryl group represented by $R_1$ is preferably selected from an alkyl group, an acylamino group, a sulfonamide group, a halogen atom, or an alkoxy group. Of these, more preferable is the alkoxy group.

In Formula (I) of this invention, "M" is either a sodium atom, or a potassium atom. Especially, of these, sodium atom is preferable. In this invention, a more preferable preparation method for a sodium sulfinate is to reduce a sulfonyl chloride with sodium sulfite or sodium hydrogensulfite in the presence of disodium hydrogenphosphate.

The following are examples of the compounds represented by said Formula (I) and said Formula (II). But the compounds of the present invention are not limited only to these compounds.

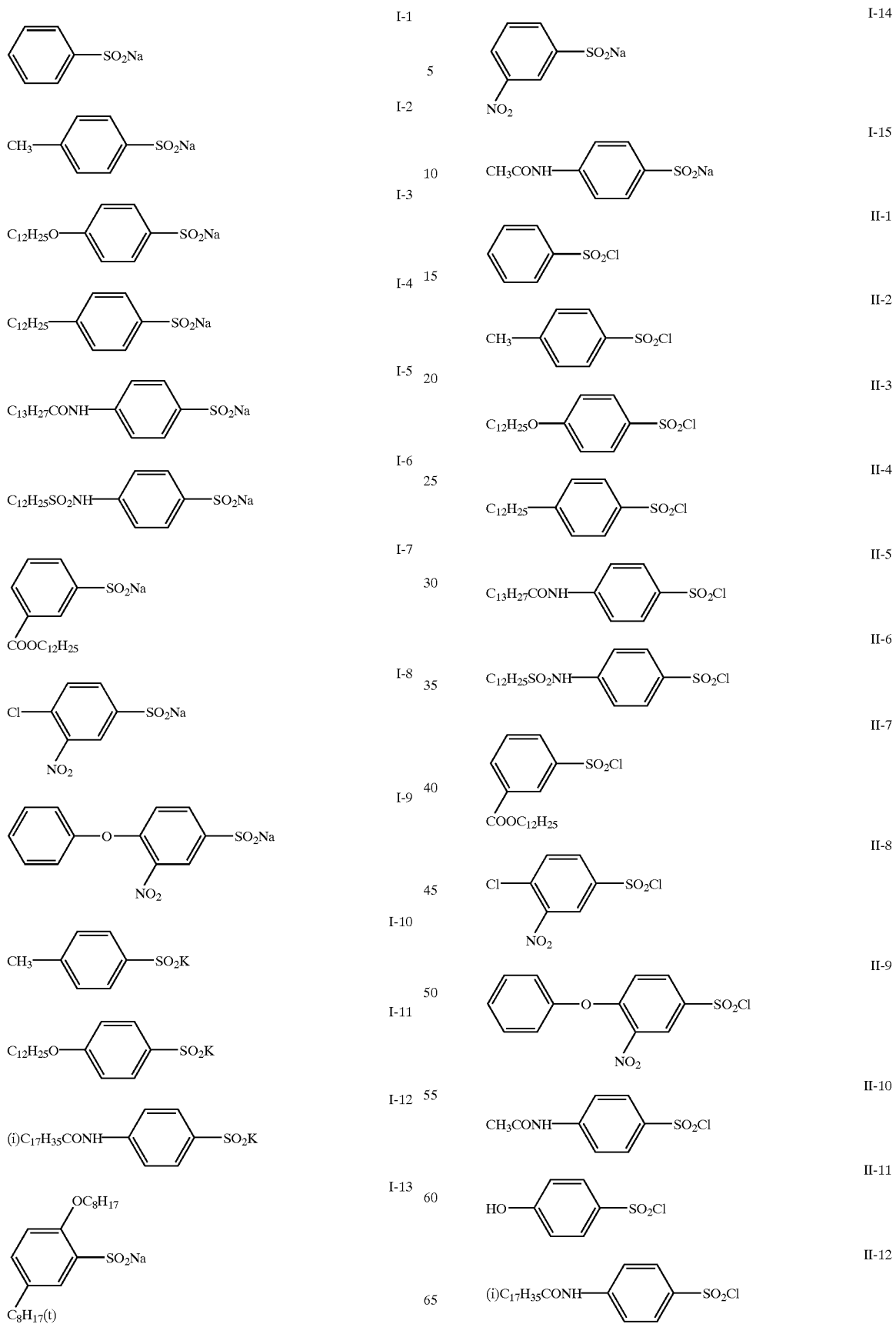

-continued

II-13
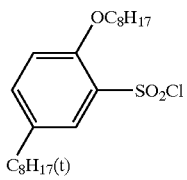

II-14
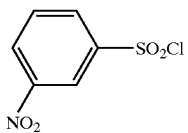

One of the most useful application of the present invention is to prepare a photographic coupler.

A photographic color coupler represented by Formula (IV) can be synthesized by a reaction of a compound represented by Formula (I) with a compound represented by Formula (III):

$R_1SO_2M$            Formula (I)

Formula (III)
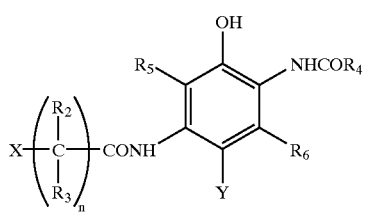

Formula (IV)
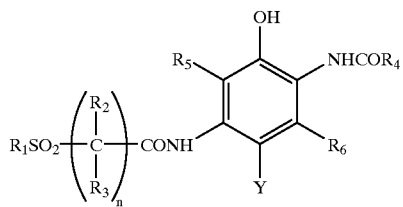

wherein $R_1$ is an aryl group; $R_2$ and $R_3$ are a hydrogen atom, an alkyl group, a cycloalkyl group, an aryl group, or a heterocyclic group; $R_4$ is an alkyl group, a cycloalkyl group, an aryl group, or a heterocyclic group; $R_5$ and $R_6$ are a hydrogen atom or a substituent; "n" is an integer of 1 to 17; "X" is a chlorine atom or a bromine atom; "Y" is a hydrogen atom, a halogen atom or a substituent that can be eliminated after reacting with an oxidized color developing agent.

Details of the compounds represented by Formula (III) and Formula (IV) are explained hereunder.

The aryl group represented by $R_1$ in Formula (III) and Formula (IV) of the invention is the same as that in Formula (I) and Formula (II) The aryl group represented by $R_1$ can however have further a substituent. Said substituent may be the same as the above-mentioned substituent for aryl group of $R_1$ in Formula (I) The aryl group represented by $R_1$ preferably has a substituent. More preferable is a substituent having an alkyl group with a carbon atom number of 8–21. The substituent of the aryl group represented by $R_1$ is preferably selected from an alkyl group, an acylamino group, a sulfonamide group, a halogen atom, or an alkoxy group. Of these, more preferable is the alkoxy group.

$R_2$ and $R_3$ represent a hydrogen atom, an alkyl group, a cycloalkyl group, an aryl group or a heterocylic group. A preferable alkyl group has a carbon atom number of 1–21, and it can be either a straight chain or a branched chain. Examples of straight chains are; a methyl group, an ethyl group, a propyl group, an octyl group, and a dodecyl group. Examples of branched chains are; an isopropyl group, a tert-butyl group, and a 2-ethylhexyl group. A preferable cycloalkyl group has a carbon atom number of 3–12, and it may have a branched structure. Examples of cycloalkyl groups are; a cyclopropyl group, a cyclopentyl group, a cyclohexyl group, a 2-methylcyclopropyl group and an adamantyl group. Examples of aryl groups are; a substituted or unsubstituted phenyl group. Heterocyclic groups are preferably 5–7 membered cycles. Examples of heterocyclic groups are; a 2-furyl group, a 2-thienyl group, a 2-pyridyl group, a 2-pyrimidinyl group, a 2-benzothiazolyl group, a 1-pyrrolyl group, and a tetrazolidinyl group.

An alkyl group, a cycloalkyl group, an aryl group, or heterocyclic group represented by $R_2$ and $R_3$ can have further a substituent. Said substituent may be the same as the above-mentioned substituent for the aryl group of $R_1$ in Formula (I) and Formula (II).

$R_2$ and $R_3$ are preferably a hydrogen atom or an alkyl group. $R_4$ represents an alkyl group, a cycloalkyl group, an aryl group or a heterocyclic group. Said alkyl group, cycloalkyl group, aryl group and heterocyclic group represented by $R_4$ indicate the same as those represented by $R_2$ and $R_3$. Said alkyl group, cycloalkyl group, aryl group and heterocyclic group represented by $R_4$ can have further a substituent, which can be the same as those indicated for the substituent of the aryl group in Formula (I) and Formula (II).

$R_5$ and $R_6$ represent a hydrogen atom or a substituent. Said substituent is the same as those indicated for the substituent of the aryl group in Formula (I) and Formula (II). $R_5$ and $R_6$ are preferably a hydrogen atom.

"n" is an integer of 1 to 17, preferably, however, "n" is 1. When "n" is an integer greater than 2, plural $R_2$ and $R_3$ may be the same or different.

"X" represents a chlorine atom or a bromine atom, and preferably a bromine atom.

"Y" is a hydrogen atom, a halogen atom, or a substituent that can be eliminated after reacting with an oxidized color developing agent. Examples of said halogen atom are; a chlorine atom, a bromine atom, and a fluorine atom. Examples of said substituent that can be eliminated after reacting with an oxidized color developing agent are; an alkoxy group, an aryloxy group, an heterocyclic-oxy group, an acyloxy group, a sulfonyloxy group, an alkoxycarbonyloxy group, an alkylthio group, an arylthio group, or a heterocyclic-thio group.

"Y" is preferably a hydrogen atom or a halogen atom, more preferably is a halogen atom, and still more preferably is a chlorine atom.

In the present invention "M" shown in Formula (I) is preferably a sodium atom.

The following are examples of the compounds represented by Formulas (III) and (IV). But the compounds of the present invention are not limited to these compounds.

III-1 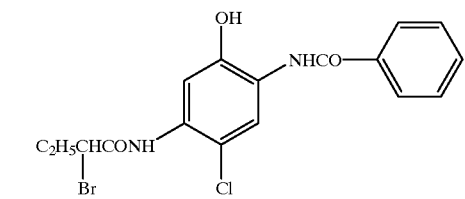
III-2 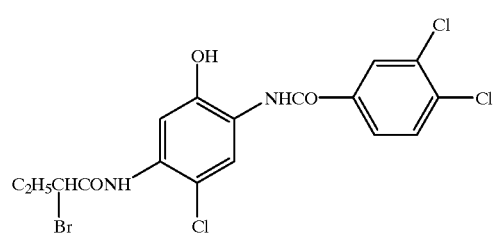
III-3 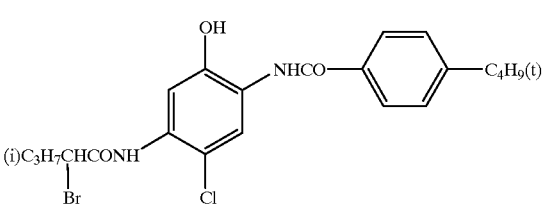
III-4 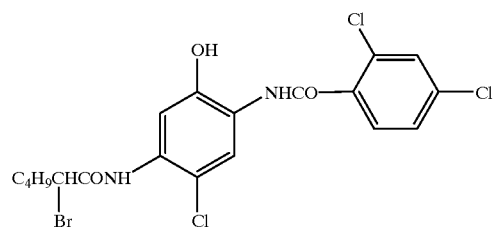
III-5 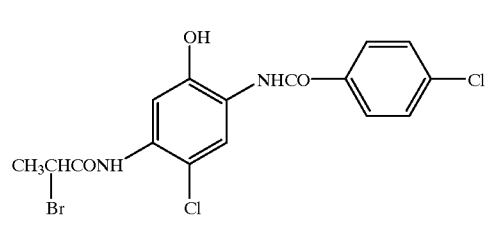
III-6 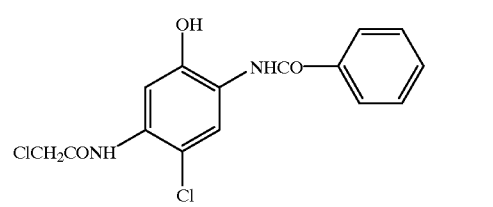
III-7 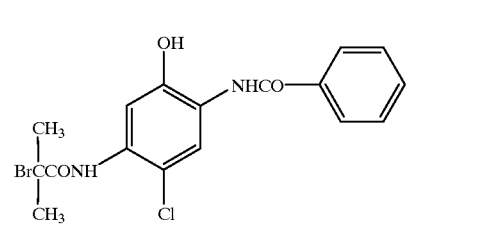
III-8 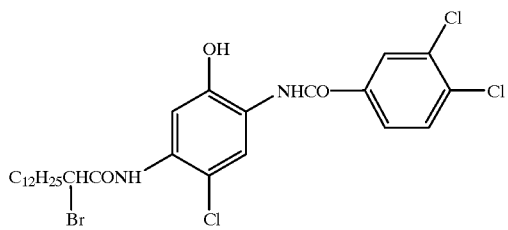
III-9 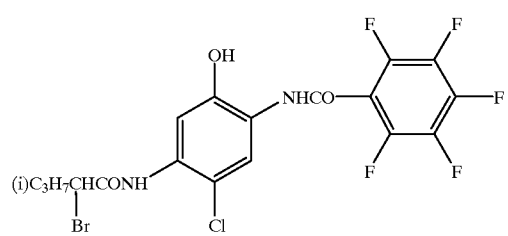
III-10 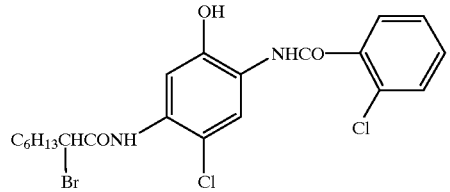
III-11 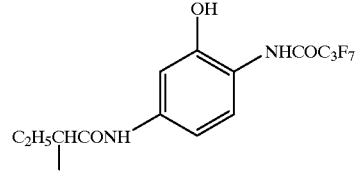
III-12 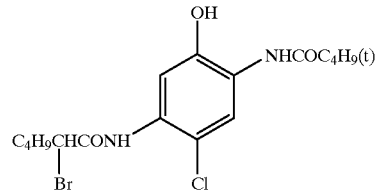
III-13 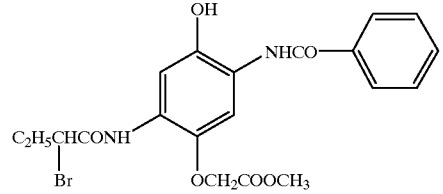
III-14 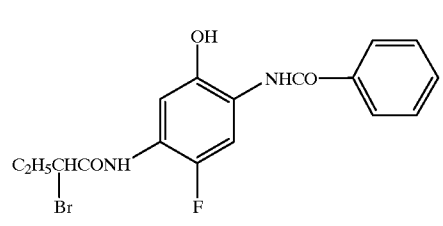

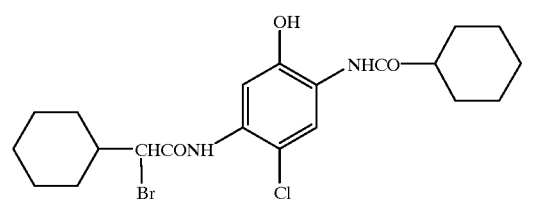
III-15
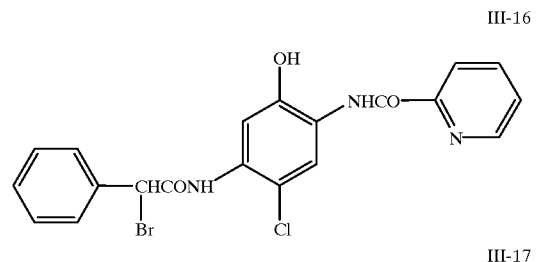
III-16
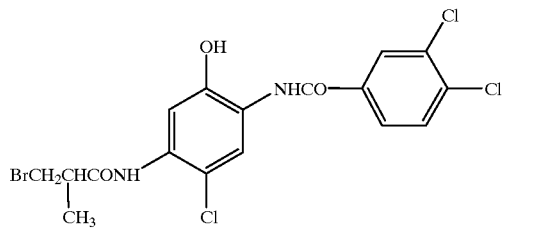
III-17
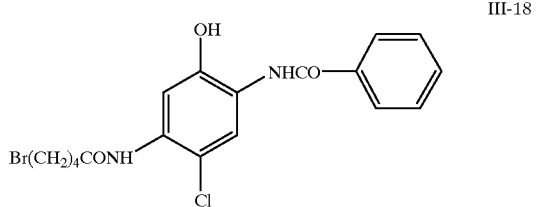
III-18
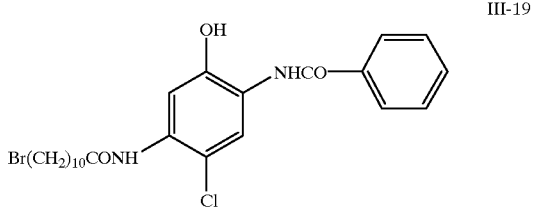
III-19
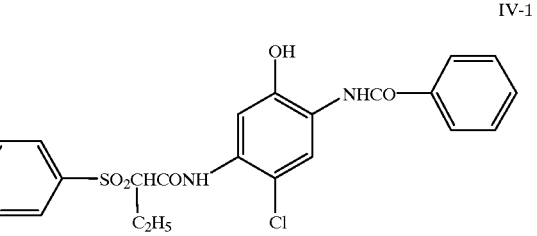
IV-1
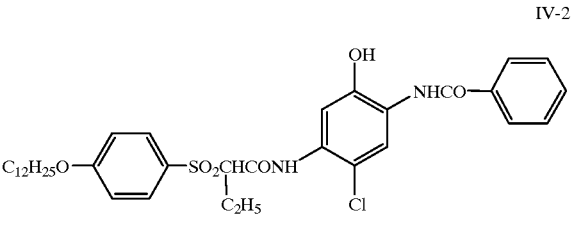
IV-2
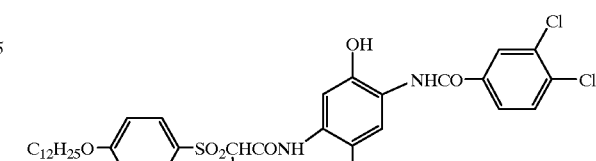
IV-3
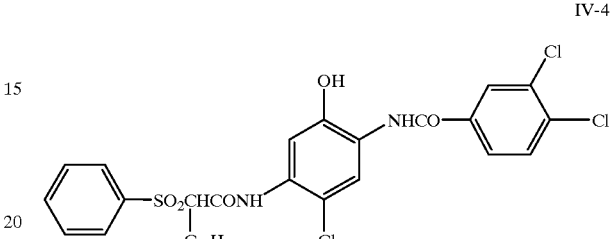
IV-4
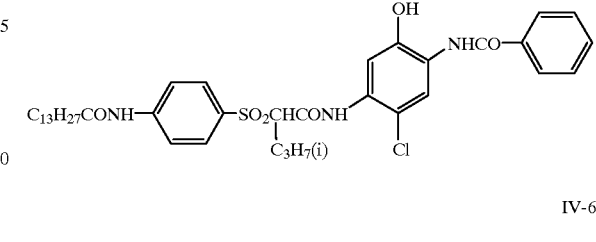
IV-5
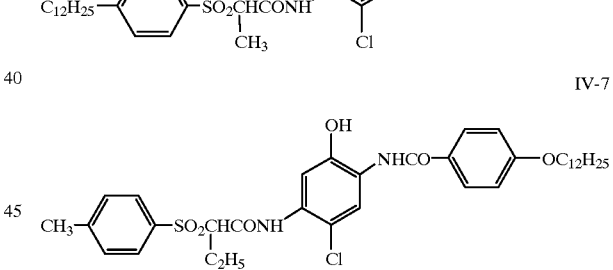
IV-6
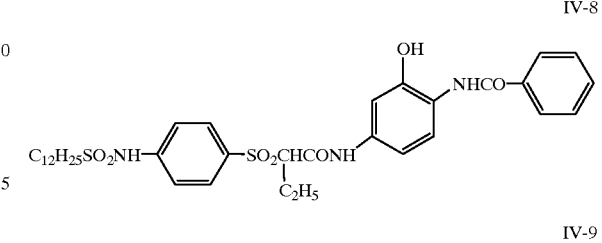
IV-7
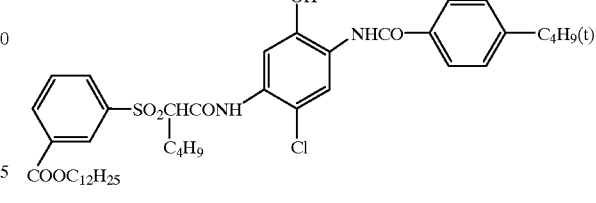
IV-8
IV-9

-continued

IV-10
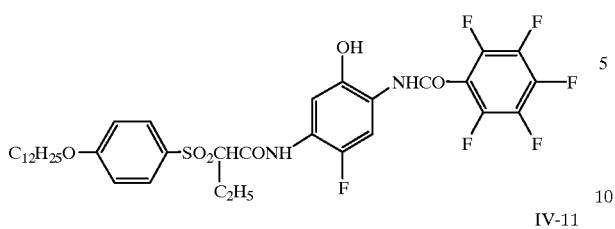

IV-17
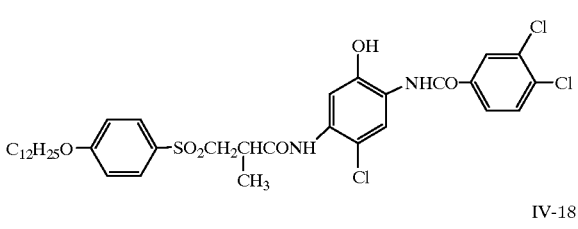

IV-11

IV-18

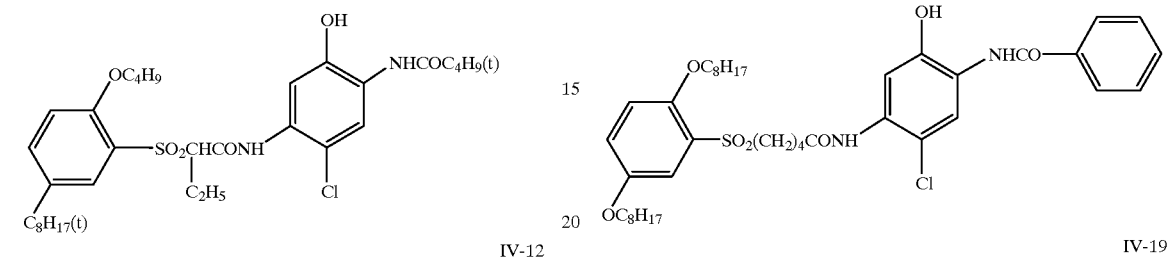

IV-12

IV-19

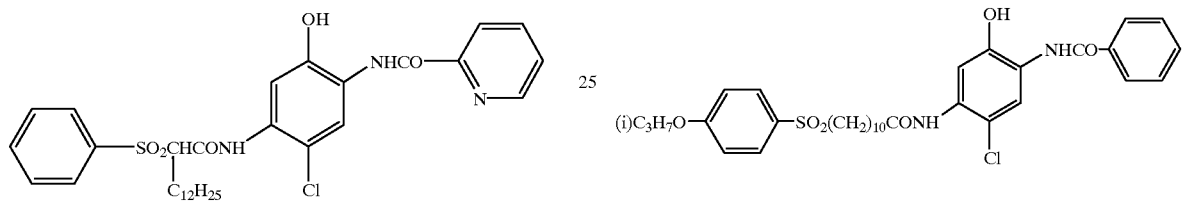

IV-13
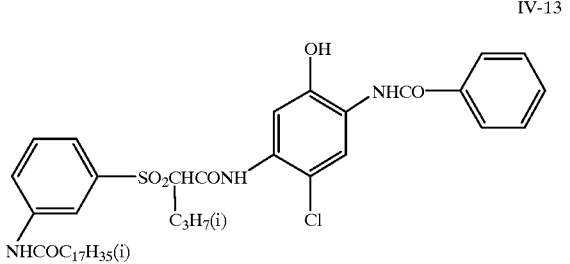

IV-14
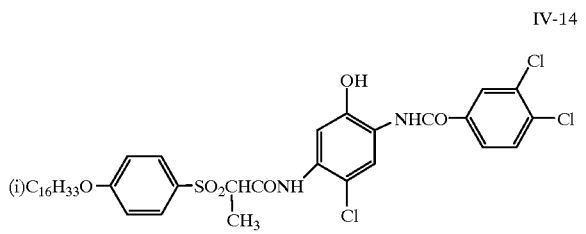

IV-15
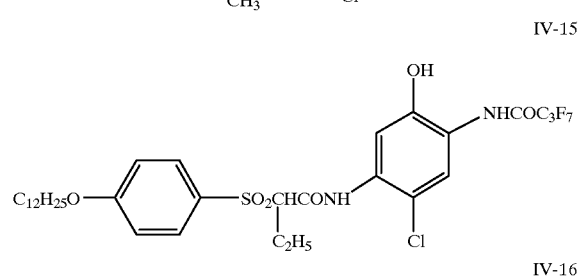

IV-16
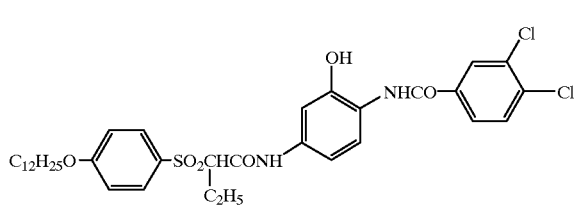

Examples of the solvent used in preparing a coupler represented by Formula (IV) of the present invention are; an alcohol type, an ester type, a halogenated type, a nitrile type, an amide type, and an aromatic hydrocarbon type. A mixture of these solvents may also be used. Of said solvents, an alcohol type, a nitrile type, and an amide type are preferable. More specifically, ethanol, isopropanol, tert-butanol, acetonitrile, and N, N-dimethylformamide are preferred. Any of these solvents may contain water.

A reaction temperature in preparing a coupler represented by Formula (IV) of the present invention is usually 0–150° C., but 20–120° C. is preferred and 50–100° C. is more preferred.

In a reaction for preparing a coupler represented by Formula (IV) of the present invention, bases can be used. Said bases may be selected from both inorganic and organic bases. Examples of inorganic bases are; sodium acetate, potassium acetate, sodium hydrogencarbonate, potassium hydrogencarbonate, sodium carbonate, potassium carbonate, lithium hydroxide, sodium hydroxide, potassium hydroxide, sodium phosphate, disodium hydrogenphosphate, and sodium hydrogenphosphate. Examples of organic bases are; triethylamine, diisopropylethylamine, tetramethyldiaminopropane, N, N-dimetylaniline, N, N-dietylaniline, pyridine, diethylenetriamine, and triethylenediamine.

In a reaction for preparing a coupler represented by Formula (IV) of the present invention, phase transfer catalysts may be used. Examples of said phase transfer catalysts are quaternary ammonium salts. More specific quaternary ammonium salts are; tetramethylammonium chloride, tributylbenzylammonium chloride, tetra-n-butylainmonium bromide, tetra-n-butylammonium iodide, and trioctylmethylammonium chloride.

The present invention is explained in detail by the following Examples, but the invention is not limited only to these Examples.

EXAMPLE 1
<<Synthesis of Compound I-3>>

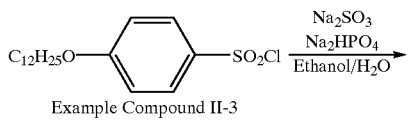

Example Compound II-3

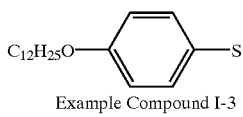

Example Compound I-3

Sodium sulfite (69.8 g, 0.554 mol) and disodium hydrogenphosphate (82.6 g, 0.582 mol) were added to 410 ml of water and then stirred. After dissolution of the salts, ethanol (105 ml) and Compound II-3 (100 g, 0.277 mol) were added and then maintained at 35–40° C. for 2 hours, while stirring. When the reaction was completed, the reaction mixture was cooled to 10° C., and the precipitated solid was collected by filtration. The obtained solid was washed with water and ethyl acetate to produce the target Compound I-3 at reaction yield of 85.3% (82.4 g).

The structure of Compound I-3 was identified with mass spectrometry and NMR spectrometry. Its purity was determined employing high-performance liquid chromatography, which revealed a purity of 99.5%.

<<Synthesis for Comparison>>

Disodium hydrogenphosphate used in the above-mentioned synthesis of Compound I-3 was replaced by, (1) the same molar amount of sodium hydroxide, and by (2) the same molar amount of sodium hydrogencarbonate. After carrying out the reactions, the yield and purity of Compound I-3 were determined. The results were: (1) 81.7% (yield), 89% (purity); (2) 77.8% (yield), 97.0% (purity). In case of sodium hydrogencarbonate, vigorous foam formation occurred which hindered smooth operation of the process.

EXAMPLE 2
<<Synthesis of Compound I-12>>

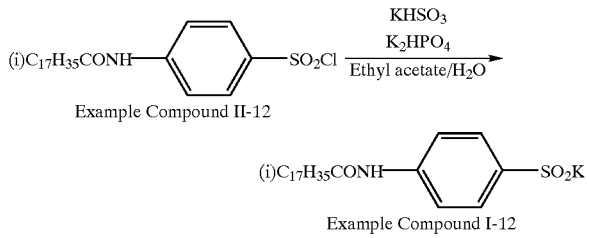

Potassium hydrogensulfite (49.8 g, 0.414 mol) and potassium hydrogenphosphate (148 g, 0.850 mol) were added to 600 ml of water and then stirred. After dissolution of the salts, ethyl acetate (100 ml) and Compound II-12 (95 g, 0.207 mol) were added and then maintained at 35–40° C. for 2 hours while stirring. When the reaction was completed, the reaction mixture was cooled to 10° C., and the precipitated solid was collected by filtration. The obtained solid was washed with water and ethyl acetate to produce the target Compound I-12 (79.1 g), yielding 82.6%.

The structure of Compound I-12 was identified with mass spectrometry and NMR spectrometry. Its purity was determined employing high-performance liquid chromatography, yielding a purity of 99.0%.

EXAMPLE 3
<<Synthesis of Compound IV-1>>

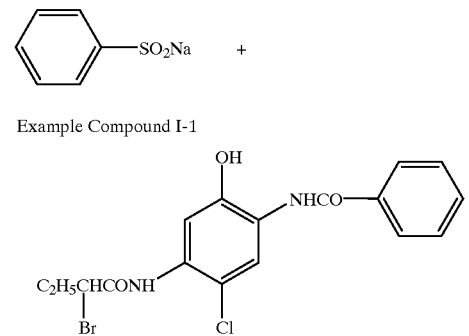

Example Compound I-1

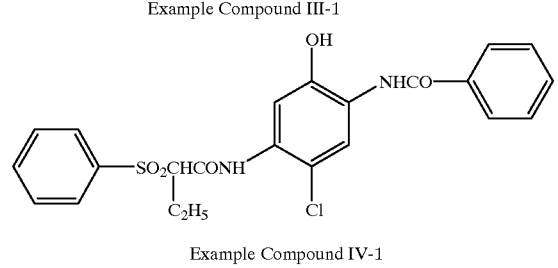

Example Compound III-1

Example Compound IV-1

Two molecular hydrous Compound I-1 (5.3 g) and Compound III-1 (10.0 g) were added to 50 ml of N, N-dimethylformamide and stirred at 95–100° C. for 2 hours. After completion of the reaction, the reaction mixture was left to cool to room temperature. Then 100 ml of ethyl acetate and 100 ml of water were added. The reaction mixture was stirred and left undisturbed after which the separated aqueous layer was discarded. The obtained ethyl acetate layer was washed three times using an aqueous solution of sodium chloride. The aqueous layer was again discarded, and then the ethyl acetate solution was evaporated under reduced pressure. The residue was purified with column chromatography (carrier: silica gel; eluent: ethyl acetate/n-hexane=2/3 (in volume)) and was further recrystallized from acetonitrile. The amount of the target Compound IV-1 was 9.7 g at a yield of 84.4%.

The structure of Compound IV-1 was identified with mass spectrometry and NMR spectrometry, and revealed a melting point of 209–210° C.

EXAMPLE 4
<<Synthesis of Compound IV-2>>

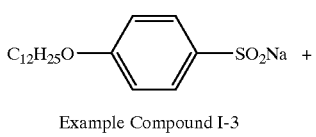

Example Compound I-3

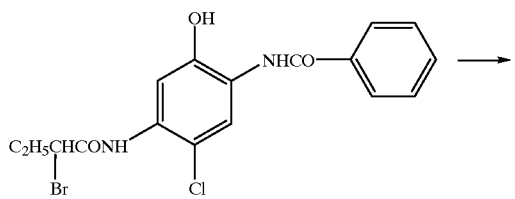

Example Compound III-1

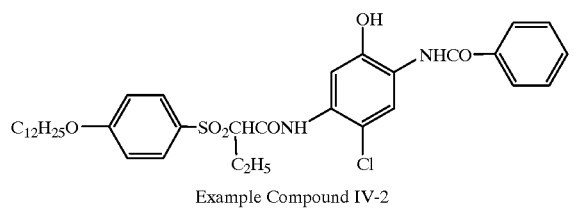

Example Compound IV-2

Compound I-3 (4.0 g) and Compound III-1 (4.3 g) were added to 50 ml of N, N-dimethylformamide and stirred at 90–95° C. for 2 hours. After completion of the reaction, the reaction mixture was left to cool to room temperature. Then, 100 ml of ethyl acetate and 100 ml of water were added. The reaction mixture was stirred and left undisturbed. The resulting separated aqueous layer was discarded. The obtained ethyl acetate layer was washed three times with an aqueous solution of sodium chloride. The aqueous layer was again discarded, and then the ethyl acetate solution was evaporated under reduced pressure. The residue was purified with column chromatography (carrier: silica gel; eluent: ethyl acetate/n-hexane=1/2 (in volume)) and was further recrystallized from acetonitrile. The amount of the target Compound IV-2 was 6.0 g, at a yield of 87.4%.

The structure of Compound IV-1 was identified with mass spectrometry and NMR spectrometry and revealed a melting point of 144–145° C.

What is claimed is:

1. A process for preparing a sulfinate through reduction of a sulfonyl chloride with a sulfite or a hydrogensulfite, in the presence of a hydrogenphosphate, wherein the sulfinate is represented by Formula (I) and said sulfonyl chloride is represented by Formula (II), $R_1SO_2M$  Formula (I)

wherein $R_1$ is an aryl group; M is a sodium atom or a potassium atom, and $R_1SO_2Cl$  Formula (II)

wherein $R_1$ is an aryl group.

2. The process of claim 1 wherein the reduction is accomplished in a mixture of at least one organic solvent and water.

3. The process of claim 1 wherein said sulfinate represented by Formula (I) is one selected from the group consisting of I-1 to I-15.

I-1

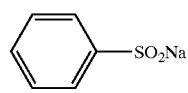

I-2

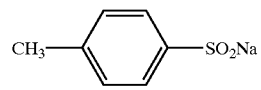

I-3

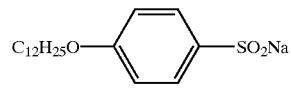

I-4

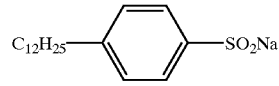

I-5

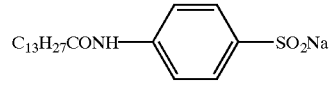

I-6

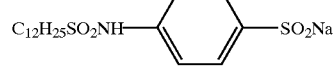

I-7

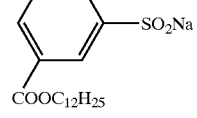

I-8

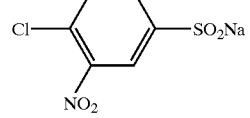

I-9

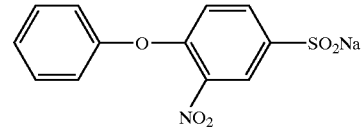

I-10

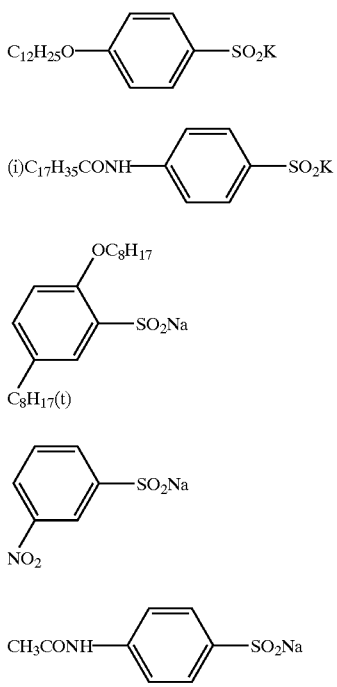

4. The process of claim 1 wherein said sulfonyl chloride represented by Formula (II) is one selected from the group consisting of II-1 to II-14.

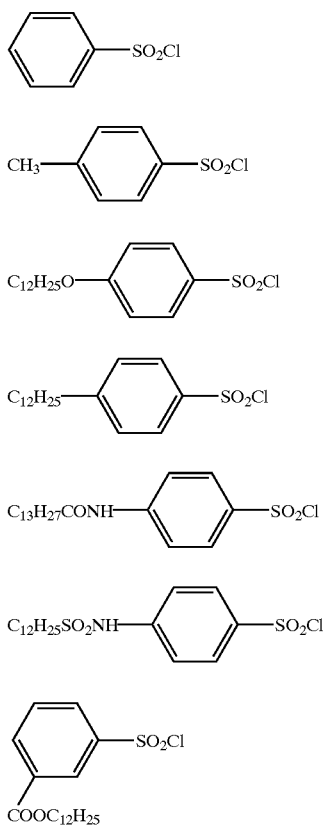

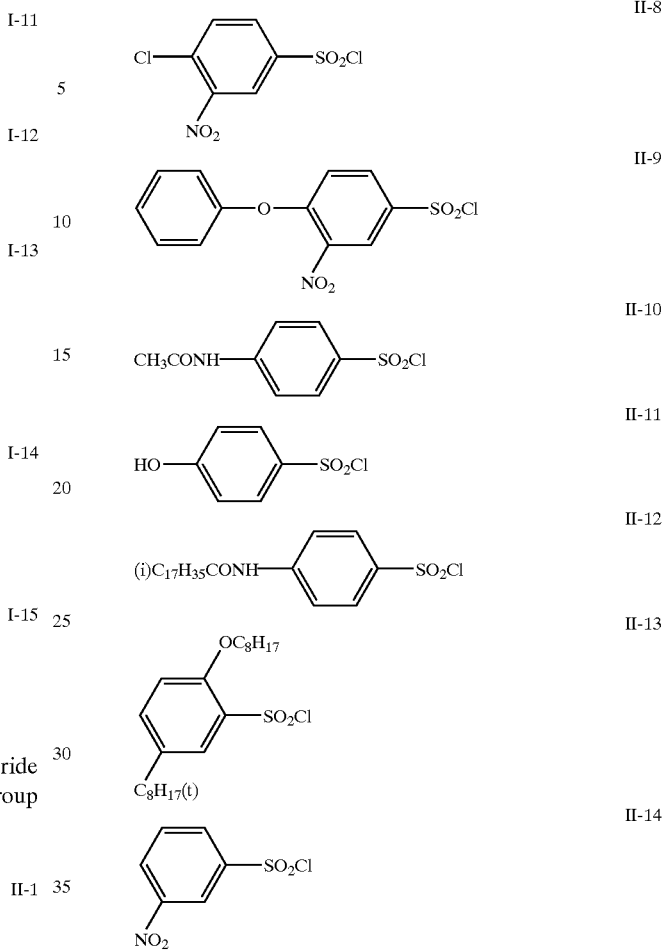

5. The process of claim 2 wherein the organic solvent is at least one selected from the group consisting of methanol, ethanol, isopropanol, butanol, tert-butanol, acetonitrile, ethyl acetate, toluene, dichloromethane, tetrahydrofuran, acetone, and N,N-dimethylformamide.

6. The process of claim 5 wherein the organic solvent is at least one selected from the group consisting of ethanol, isopropanol, tert-butanol, and acetonitrile.

7. A process for preparing a sulfinate through reduction of a sulfonyl chloride with a sulfite or a hydrogensulfite, in the presence of a hydrogenphosphate, wherein the sulfinate is represented by Formula (I), $$R_1SO_2M \qquad \text{Formula (I)}$$

wherein $R_1$ is an aryl group; M is a sodium atom or a potassium atom.

8. The process of claim 7 wherein the reduction is accomplished in a mixture of at least one organic solvent and water.

9. The process of claim 7 wherein said sulfonyl chloride is represented by Formula (II), $$R_1SO_2Cl \qquad \text{Formula (II)}$$

wherein $R_1$ is an aryl group.

10. The process of claim 7 wherein said sulfinate represented by Formula (I) is one selected from the group consisting of I-1 to I-15.

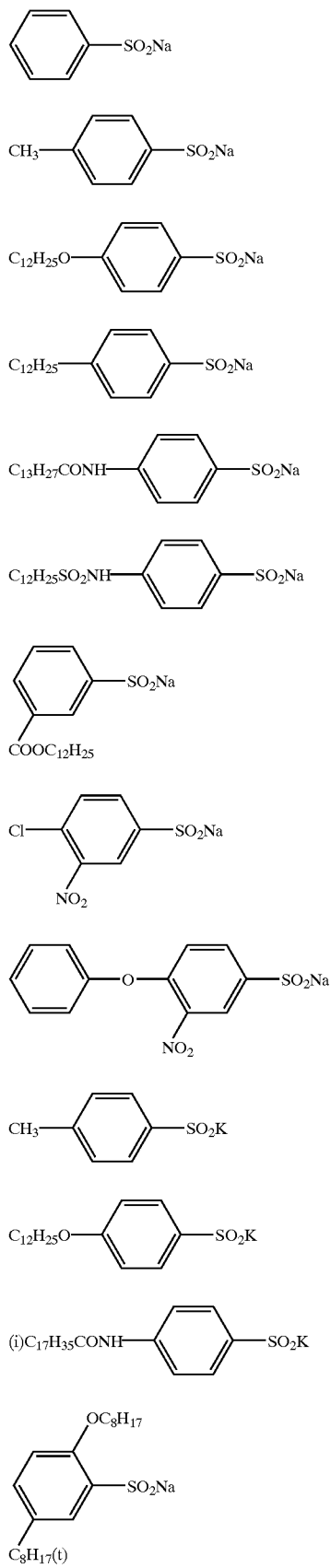
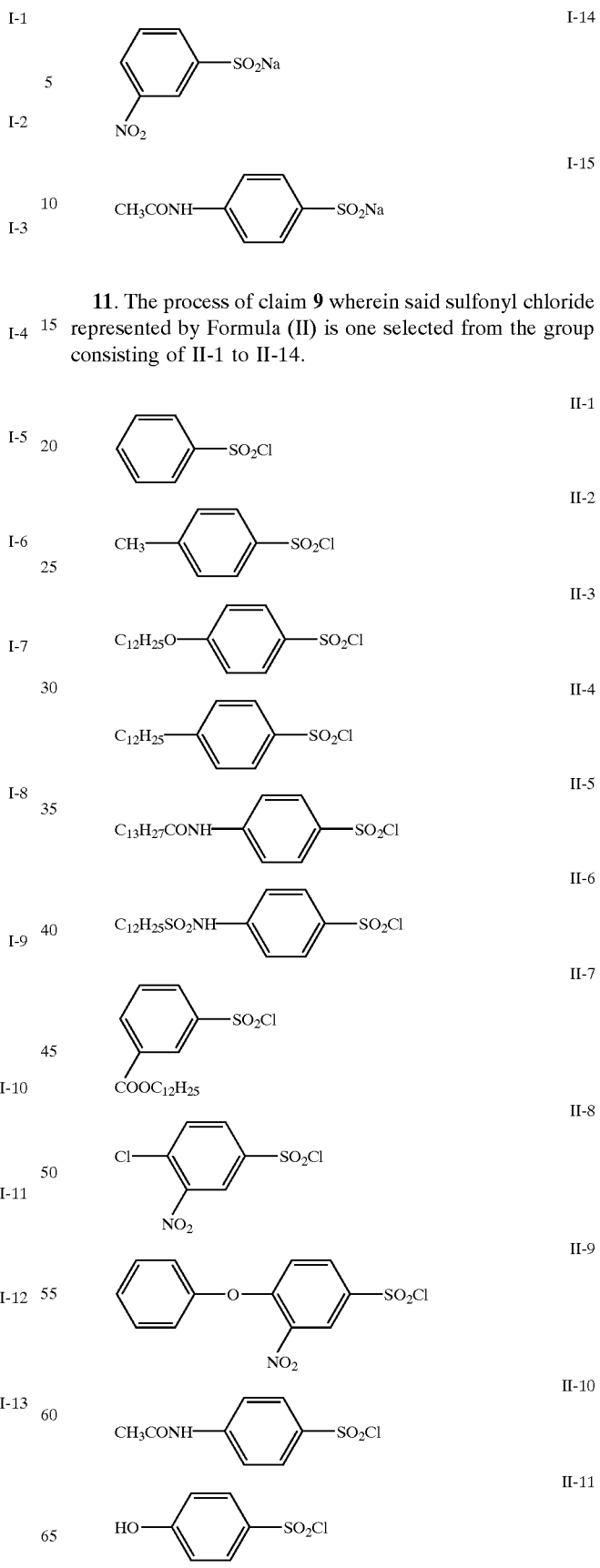
11. The process of claim 9 wherein said sulfonyl chloride represented by Formula (II) is one selected from the group consisting of II-1 to II-14.

-continued

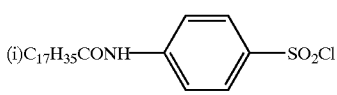
II-12

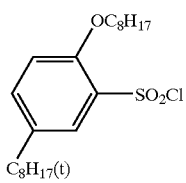
II-13

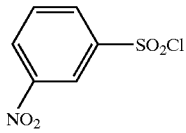
II-14

12. The process of claim 8 wherein the organic solvent is at least one selected from the group consisting of methanol, ethanol, isopropanol, butanol, tert-butanol, acetonitrile, ethyl acetate, toluene, dichloromethane, tetrahydrofuran, acetone, and N, N-dimethylformamide.

13. A process for preparing an aryl sulfinate through reduction of a sulfonyl chloride with a sulfite or a hydrogensulfite, in the presence of a hydrogenphosphate wherein said sulfonyl chloride is represented by Formula (II), $$R_1SO_2Cl \qquad \text{Formula (II)}$$

wherein $R_1$ is an aryl group.

14. The process of claim 13 wherein the reductiion is accomplished in a mixture of at least one organic solvent and water.

15. The process of claim 13 wherein the sulfinate is represented by Formula (I), $$R_1SO_2M \qquad \text{Formula (I)}$$

wherein $R_1$ is an aryl group; M is a sodium atom or a potassium atom.

16. The process of claim 15 wherein said sulfinate represented by Formula (I) is one selected from the group consisting of I-1 to I-15.

I-1

I-2

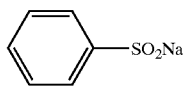
I-3

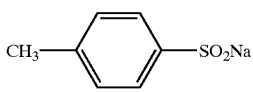
I-4

-continued

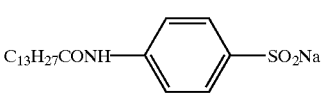
I-5

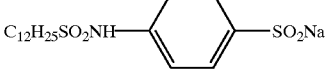
I-6

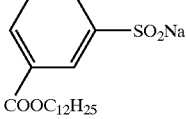
I-7

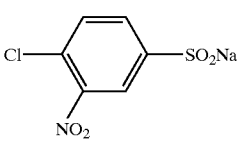
I-8

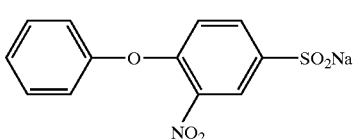
I-9

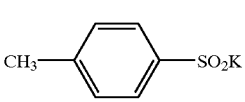
I-10

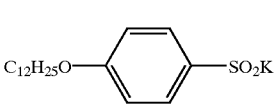
I-11

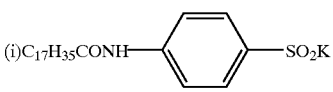
I-12

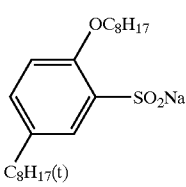
I-13

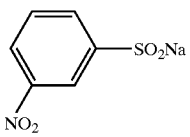
I-14

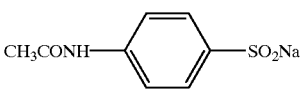
I-15

17. The process of claim 13 wherein said sulfonyl chloride represented by Formula (II) is one selected from the group consisting of II-1 to II-14.

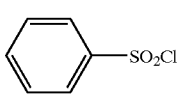
II-1

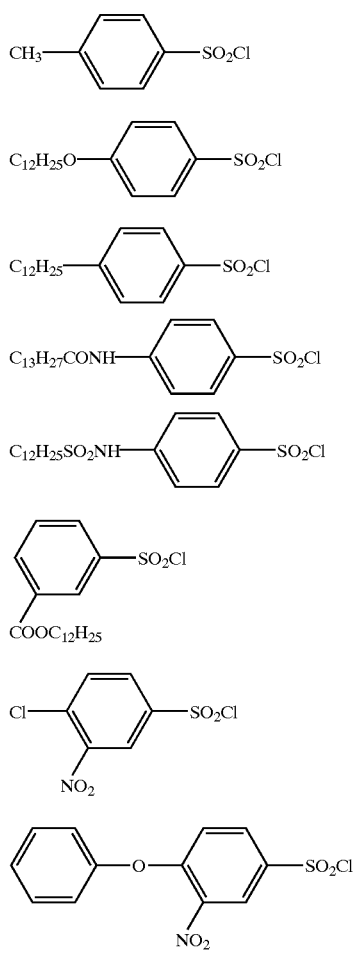
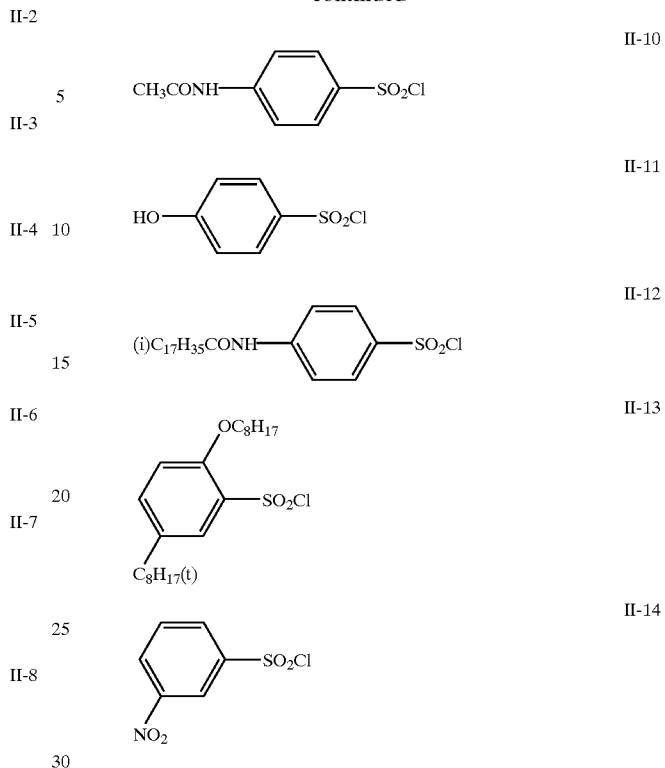
18. The process of claim 14 wherein the organic solvent is at least one selected from the group consisting of methanol, ethanol, isopropanol, butanol, tert-butanol, acetonitrile, ethyl acetate, toluene, dichloromethane, tetrahydrofuran, acetone, and N,N-dimethylformamide.
* * * * *